United States Patent [19]

Ware et al.

[11] 4,248,247
[45] Feb. 3, 1981

[54] LOW COST POST-OPERATIVE ELECTRODE

[75] Inventors: Lyle A. Ware, Bloomington; Marc D. Noerenberg, Chaska, both of Minn.

[73] Assignee: Med General, Inc., Minneapolis, Minn.

[21] Appl. No.: 52,930

[22] Filed: Jun. 28, 1979

[51] Int. Cl.³ .................................................. A61B 5/04
[52] U.S. Cl. ...................................... 128/798; 128/802
[58] Field of Search ............................... 128/639–641, 128/644, 783, 798, 802, 803

[56] References Cited

U.S. PATENT DOCUMENTS

| | | | |
|---|---|---|---|
| 3,817,252 | 6/1974 | Maurer | 128/798 |
| 3,972,329 | 8/1976 | Kaufman | 128/641 |
| 4,141,366 | 2/1979 | Cross, Jr. et al. | 128/640 |

FOREIGN PATENT DOCUMENTS 1965195  7/1971  Fed. Rep. of Germany ............ 128/640

Primary Examiner—Lee S. Cohen
Attorney, Agent, or Firm—Orrin M. Haugen; Thomas J. Nikolai

[57] ABSTRACT

A low-cost, disposable electrode for body surface stimulating applications having a backing layer formed from a sheet of foamed plastic material which is generally divided into two halves by a transversely extending fold line. The first half has an opening extending through the thickness dimension thereof and on a surface of the second half is adhesively affixed a flexible, conductive sheet which is so positioned that when the backing layer is folded along the fold line, the flexible conductive sheet fits through the opening formed on the first half. Completing the assembly is a layer of conductive adhesive which is affixed to the undersurface of the foamed plastic layer so as to abut the surface of the flexible conductive sheet exposed through the opening and an electrical lead connected to the flexible conductive sheet.

6 Claims, 1 Drawing Figure

U.S. Patent  Feb. 3, 1981  4,248,247
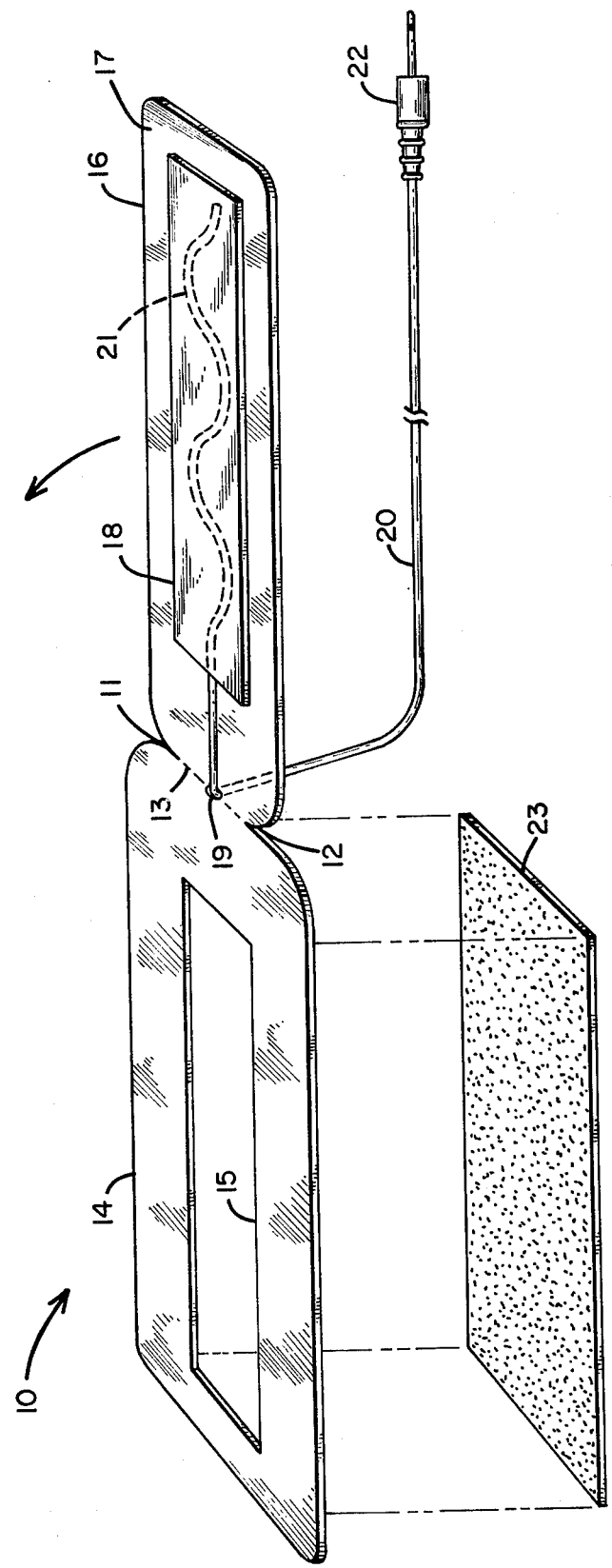

LOW COST POST-OPERATIVE ELECTRODE

BACKGROUND OF THE INVENTION

I. Field of the Invention

This invention relates generally to electrode structures useful in applying electrical stimulating impulses to the body of a patient and more particular to an improved construction of such an electrode structure which provides improved flexibility without a corresponding sacrifice in the area of current distribution. As such, patient mobility is enhanced and so-called hot spots are avoided.

II. Description of the Prior Art

It has become well recognized that the application of pulse-type electrical stimulating signals to the body of a patient can produce generally therapeutic effects. For example, many forms of transcutaneous nerve stimulators are now available for use in the medical field. For example, in the Hagfors et al U.S. Pat. No. 3,911,930, there is described a body stimulating apparatus for ameliorating post-operative pain. The apparatus comprises a pulse generator which is adapted to be coupled to the body of the patient by way of surface electrodes.

The present invention pertains to the improved design of such surface electrodes. In the application of electrical stimulating current impulses to the body of a patient, it is desirable that the electrode structure be extremely flexible so as to conform to the skin surface of the patient, irrespective of the body motions which may take place at the electrode site. Furthermore, the goal of increased mobility must not be accompanied by an attendant inordinate increase in the current density at a localized site within the area covered by the electrode. Thus, the patient must be free to move without creating hot spots which might result in damage to the skin tissue or noxious pain.

Many forms of body electrodes are known in the art. For example, in the Kaufman U.S. Pat. No. 3,972,329, there is disclosed a disposable body electrode which is adapted to be adhesively attached to the body of the patient. It comprises a backing layer and a skin surface layer which sandwiches a generally rectangular metal electrode. The structure is designed to be adhesively secured to the patient's body. The conductive metal electrode portion of this structure comprises a rectangular sheet which is to be sufficiently flexible so as to conform to the contours of the body. Irrespective of the thickness of such metal electrode, as the surface area to be treated increases, there is a propensity for hot spots to develop should the electrode structure be bent or folded as by motion of the patient.

The invention of the Maurer U.S. Pat. No. 3,817,252 attempts to resolve this problem by utilizing a metal screen or mesh to achieve greater current distribution while maintaining a reasonable degree of flexibility to the electrode structure. A backing layer is provided having a terminal pin passing therethrough. The conductive screen is in electrical contact with the terminal pin and this screen is overlaid with a so-called diffuser screen. The skin interface pad overlaying the diffuser screen then completes the electrode structure.

SUMMARY OF THE INVENTION

The present invention is deemed to be an improvement over the electrode structures described in the above-referenced Kaufman and Maurer Patents. Specifically, the present invention provides a low-cost, disposable electrode structure for use with transcutaneous nerve stimulating apparatus in that electrodes made in accordance with the teachings of the present invention are highly flexible and thereby conform to the contours of the patient, irrespective of the positions or motions assumed by the patient, while still providing a relatively large electrode surface area which serves to maintain the current density at values below that which would tend to cause burns or other damage to the skin membranes.

The electrode structure made in accordance with the teachings of the present invention incorporate a generally rectangular backing layer which is preferably formed from a sheet of foamed plastic material. In the early stages of manufacture of the electrode structure, the foamed plastic material is a continuous flat sheet approximately twice the length of the finished electrode, the sheet being arranged to be folded along a transversely extending median line. On one side of the median line the sheet is provided with a generally rectangular opening extending through the thickness dimension of the sheet. Symmetrically disposed on the other half of the backing sheet is a thin, flexible, conductive rubber sheet which is dimensioned so that when the backing layer is folded along the transversely extending median line, the conductive rubber sheet passes through the opening formed in the first half of the backing layer member. An electrical lead in the form of an insulated wire passes through a small aperture formed proximate the median line, an uninsulated portion of the wire contacting the conductive rubber sheet or pad. Completing the electrode structure of the preferred embodiment is a sheet of conductive adhesive material which is laminated to the underside of the half of the backing layer containing the opening. As such, the conductive adhesive layer abuts the conductive rubber sheet and provides a broad surface area substantially coextensive with the dimensions of the backing layer itself.

As will be more fully set forth when the preferred embodiment is described, the electrode structure of the present invention can be fabricated using a laminating process requiring very little in the way of manual intervention. As such, the manufacture of the electrode structure can be done at very low cost. The use of a conductive adhesive for affixing the electrode to the skin of the patient permits a maximum conductive to adhesive area ratio. Then too, the folded, laminated construction with a recess for receiving the conductive rubber pad, provides a thin cross-section for high flexibility. Further, the use of conductive rubber to diffuse the electrical stimulating currents to a large area on the conductive adhesive prevents "hot spots" due to its built-in resistivity. The solid conductive rubber also prevents "bleed through" of copper ions (or other noxious ions) into the conductive adhesive and into to the skin.

Because the electrode structure, when formed in accordance with the foregoing design approach, is extremely flexible when it is adhesively attached to the skin of the patient, it is able to conform to the body contours of the patient as he moves about. In that the effective electrode area is coextensive with the conductive adhesive layer used to affix it to the patient's body, it is possible to design an electrode which limits the current density when pulse type signals are applied to it. As such, the problem of so-called "hot spots" are obviated and the electrode may continue to be worn by the patient over prolonged periods of time without fear of burning or irritation.

In packaging the electrode structure for sale and distribution, it has also been found expedient to employ a removable plastic release layer which abuts the exposed surface of the conductive adhesive layer. The doctor or patient, when utilizing the electrode structure of the present invention, merely has to peel off the release layer to thereby expose the adhesive surface. The electrode is then placed upon the body of the patient at a desired locaton and is held in place by the conductive adhesive material.

OBJECTS

It is accordingly a principal object of the present invention to provide a new and improved disposable body electrode for use with a transcutaneous nerve stimulator device.

Another object of the invention is to provide a low-cost electrode structure which is highly flexible, while still maintaining a desired current distribution over an extended area.

Yet another object of the invention is to provide an electrode structure having a foamed plastic backing layer which is effectively divided into two halves about a transversely extending fold line, with a flexible conductive pad affixed to a surface of one of the halves so that when the fold is made, this pad will extend through an opening formed in the other half of the backing layer so as to conductively engage a thin layer of a conductive adhesive material ultimately used to affix the electrode structure to the body of the patient.

These and other objects and advantages of the invention will become apparent to those skilled in the art from the following detailed description of the preferred embodiment when considered in light of the accompanying drawings in which is illustrated the construction of the preferred embodiment.

DESCRIPTION OF THE PREFERRED EMBODIMENT

Referring to the drawing which shows in an exploded presentation the structure comprising the disposable body electrode forming the preferred embodiment of the present invention.

There is identified by numeral 10 a generally rectangular, flexible, insulating sheet member having notches 11 and 12 extending inwardly from the side edges thereof and defining a transversely extending fold line which is indicated by the dashed line 13. The flexible insulating sheet 10 is preferably formed from a foamed plastic material such as foamed polyethylene which may typically be 1/16th inch in thickness and may have an overall width of approximately 2½ inches. Other dimensions are, of course, usable and accordingly no limitations are intended. The sheet 10, when folded along the line 13 may have an overall length in the range of from 9 to 12 inches.

When viewed as in the drawing, the left half 14 of the backing layer 10 has centrally disposed in it a generally rectangular aperture or opening 15 which may conveniently be formed in a stamping operation. The right half 16 of the backing layer 10 is coated with a suitable adhesive and disposed upon the upper surface 17 thereof is a generally rectangular, thin, flexible strip 18 of a conductive material. The conductive strip 18 is preferably formed from a synthetic plastic material such as rubber which is impregnated with electrically conductive particles such as carbon or the like.

A generally circular aperture 19 is formed through the backing layer 10 proximate the center of the fold line 13. Passing through this aperture is an insulated conductor 20 which may have a pin-type connector 22 at its proximal end. The distal end of the conductor 20 has the insulation stripped therefrom and is sandwiched between the abutting surfaces of the conductive strip 18 and the surface 17 of the backing layer as represented by the broken lines 21.

Because of the symmetrical location of the opening 15 on the left half 14 of the backing member and the strip 18 on the right half 16 of the same backing member, when the assembly is folded along the fold line 13, the strip 18 will pass through the opening 15 so that the exposed surface thereof will now be substantially coplanar with the underside of the backing layer half 14.

Completing the assembly is a conductive adhesive layer or member 23 which is bonded to the underside of the left half 14 of the backing layer 10. When this bonding step is completed, good electrical contact is maintained between the flexible conductive strip 18 and the conductive adhesive layer 23. The material used to fabricate the conductive adhesive layer 23 is that set out in the co-pending Lyle A. Ware et al application Ser. No. 49,212, filed June 15, 1979 and entitled Flexible Self-Adhesive Bio-Electrodes, which application is assigned to the assignee of the present application. Because the composition and manner of formulating the conductive adhesive layer is fully set out in that application, it is deemed unnecessary to include such descriptive material herein, it being understood that the teachings of the aforereferenced Ware et al application are incorporated by reference herein.

While for purposes of explanation, the electrode structure is illustrated in the drawing in an exploded view format, it is to be understood that in use, the conductive adhesive layer 23 is adhesively secured to the underside of the foamed layer 10 within the borders of the leftmost half 14 thereof. Similarly, the flexible conductive strip 18 is adhesively bonded to the surface 17 of the right half of the foamed layer 10 with the uninsulated portion 21 of the lead 20 sandwiched therebetween. The backing layer 10 is also folded about the fold line 13 such that the strip 18 passes through the opening 15 formed in the backing layer half 14. While not shown in the drawing, a suitable release paper may also be provided on the undersurface of the layer 23 to facilitate packaging and handling. Thus, preparatory to the application of the electrode to the body of the patient, the doctor or patient can insert his thumb nail between the bottom of the foam layer 10 and the sheet of release paper (not shown) and can peel back the release paper so as to expose the body contacting conductive adhesive layer 23.

The pin connector 22 on the proximal end of the lead 20 is adapted to be connected to a transcutaneous electrical nerve stimulator or pulse generator which applies electrical stimulating impulses of a desired amplitude, width and repetition rate to the patient. The impulses are conductive over the insulated lead 20 to the conductive rubber pad 18. Because the pad 18 is in intimate contact with the conductive adhesive layer 23, the effective surface area of the electrode is that determined by the length and width dimension of the layer 23. Thus, a uniform current density can be maintained over the area of the electrode site and hot spots are avoided.

Because the materials employed in fabricating the electrode comprising the preferred embodiment are highly flexible, the electrode adheres well to the patient's body even when the patient moves about.

Furthermore, the use of soft foam material and the conductive adhesive layer thereon to increase the effective area of the electrode offers a substantial advantage over the use of a conductive screen of the type disclosed in the prior art. The improvement resides particularly in the comfort experienced by the patient. Specifically, the sponge configuration of the present invention does not have ragged edges such as exist on a woven screen and, hence, does not cause localized sites of high current density which may cause irritation and even burning of the skin surface. Then too, the electrode structure being thin and highly flexible, readily conforms to the contours of the patient and permits the patient to move about more readily. This flexibility is accomplished without a corresponding sacrifice in current distribution area.

It is apparent that many modifications and variations of the present invention may become apparent to persons of ordinary skill in the art upon a reading of the foregoing specification in light of the accompanying drawing. Accordingly, it is to be understood, that within the scope of the appended claims, the invention may be practiced otherwise than as specifically set forth.

What is claimed is:

1. A conformable electrode for attachment to the skin of a patient comprising:
   (a) a generally rectangular sheet of flexible plastic material folded along a median line extending transverse to the longitudinal axis of said sheet so as to effectively divide said sheet into two halves;
   (b) an aperture of a predetermined size centrally disposed in one of said halves;
   (c) a flexible conductive sheet member of a predetermined dimension adhesively attached to the other of said halves and disposed within said aperture;
   (d) means for making an electrical connection to said flexible conductive sheet member; and
   (e) a continuous conductive adhesive material affixed to said one of said halves and contacting the surface of said flexible conductive sheet member which is exposed through said aperture.

2. The electrode as in claim 1 wherein said sheet of flexible plastic material is a foamed plastic.

3. The electrode as in claim 1 wherein said flexible conductive sheet member comprises a synthetic conductive rubber material.

4. The electrode as in claim 1 wherein said means for making electrical connection to said flexible conductive sheet member comprises:
   (a) an insulated conductive wire having a predetermined portion at its distal end free of insulation, said wire passing through an aperture formed proximate said median line, the uninsulated portion of the wire contacting said flexible conductive sheet member.

5. The electrode as in claim 4 wherein said conductive wire is sandwiched over a predetermined portion of its length between said other of said halves of said flexible plastic material and said flexible conductive sheet member adhesively attached thereto.

6. The electrode as in claim 1 wherein said conductive adhesive material comprises a composition having a formulation as follows:

| Ingredient | Percent by Weight |
|---|---|
| A liquid polybutene having a molecular weight of between 1,000 and 160,000; [.] | 10 to 35% |
| a [A] compatible rubber with a molecular weight of 50,000 to 350,000; [.] | 0 to 25% |
| an [An] electrically conductive polymeric filler consisting of sodium carboxymethylcellulose, pectin, and a mixture thereof; [.] | 15 to 25% |
| a [A] conductive electrolyte selected from the group consisting of sodium chloride, potassium chloride, potassium acetate, and sodium acetate and mixtures thereof; [.] | 0.3 to 0.6% |
| boric [Boric] acid; and [.] | 1 to 3% |
| water [Water] (balance) | 20 to 65%. |

* * * * *